US009687595B2

(12) United States Patent
Hensler et al.

(10) Patent No.: US 9,687,595 B2
(45) **Date of Patent: *Jun. 27, 2017**

(54) ANTI-CLOG SUCTION TIP APPARATUS AND METHOD

(71) Applicant: H & M Innovations, LLC, Wilmington, NC (US)

(72) Inventors: Robert Sean Hensler, Wilmington, NC (US); Thomas Eric Melin, Wilmington, NC (US)

(73) Assignee: H & M INNOVATIONS, LLC, Wilmington, NC (US)

(*) Notice: Subject to any disclaimer, the term of this patent is extended or adjusted under 35 U.S.C. 154(b) by 0 days.

This patent is subject to a terminal disclaimer.

(21) Appl. No.: 14/466,700

(22) Filed: Aug. 22, 2014

(65) Prior Publication Data

US 2015/0073362 A1 Mar. 12, 2015

Related U.S. Application Data

(63) Continuation of application No. 14/071,602, filed on Nov. 4, 2013, now Pat. No. 8,845,618, which is a continuation-in-part of application No. 13/680,055, (Continued)

(51) Int. Cl.

| | |
|---|---|
| ***A61M 5/00*** | (2006.01) |
| ***A61M 1/00*** | (2006.01) |
| *A61M 25/00* | (2006.01) |
| *A61M 31/00* | (2006.01) |
| *A61M 25/16* | (2006.01) |

(Continued)

(52) U.S. Cl.

CPC .......... *A61M 1/0074* (2013.01); *A61M 1/008* (2013.01); *A61M 1/0041* (2013.01); *A61M 1/0078* (2013.01); *A61M 1/0086* (2014.02); *A61M 1/0047* (2013.01)

(58) Field of Classification Search

CPC ........ A61M 5/00; A61M 25/00; A61M 31/00; A61M 25/16; A61M 39/02; A61M 27/00; A61K 9/02

See application file for complete search history.

(56) References Cited

U.S. PATENT DOCUMENTS 3,375,828 A 4/1968 Sheridan
3,958,573 A * 5/1976 Wiley .................... A61C 17/04 604/267

(Continued)

*Primary Examiner* — Tatyana Zalukaeva
*Assistant Examiner* — Ilya Treyger
(74) *Attorney, Agent, or Firm* — Tillman Wright, PLLC; Chad D. Tillman; Jeremy C. Doerre

(57) ABSTRACT

An anti-clog suction tip apparatus includes a suction tip having a suction opening and an interior defining a suction channel. An ejection wire channel extends to a wire exit opening into the suction channel that is located proximate the suction opening. An ejection wire including a ball tip at an end thereof occupies the ejection wire channel and is transitionable between a retracted configuration and an advanced configuration such that, in the retracted configuration, the ejection wire including the ball tip is retained within the ejection wire channel and does not obstruct suctioning of debris through the suction channel; and in the advanced configuration, the ball tip of the ejection wire does not extend more than three millimeters beyond the suction opening.

20 Claims, 7 Drawing Sheets

Related U.S. Application Data filed on Nov. 17, 2012, now Pat. No. 8,574,222, and a continuation-in-part of application No. 13/596,036, filed on Aug. 27, 2012, now Pat. No. 8,636,722, and a continuation-in-part of application No. PCT/US2012/052413, filed on Aug. 25, 2012, said application No. 13/680,055 is a continuation of application No. 13/596,036, filed on Aug. 27, 2012, now Pat. No. 8,636,722, which is a continuation of application No. PCT/US2012/052413, filed on Aug. 25, 2012, and application No. 13/596,036.

(60) Provisional application No. 61/527,123, filed on Aug. 25, 2011, provisional application No. 61/614,915, filed on Mar. 23, 2012, provisional application No. 61/527,123, filed on Aug. 25, 2011, provisional application No. 61/614,915, filed on Mar. 23, 2012.

(51) Int. Cl.

| | |
|---|---|
| *A61M 39/02* | (2006.01) |
| *A61M 27/00* | (2006.01) |

(56) References Cited

U.S. PATENT DOCUMENTS

| | | | | |
|---|---|---|---|---|
| 4,400,168 | A | 8/1983 | Buechel | |
| 4,699,138 | A | 10/1987 | Behrstock | |
| 5,320,110 | A | 6/1994 | Wang | |
| 5,591,141 | A | 1/1997 | Nettekoven | |
| 5,628,733 | A * | 5/1997 | Zinreich | A61M 27/00 604/267 |
| 6,146,136 | A | 11/2000 | Tenniswood | |
| 7,993,329 | B2 * | 8/2011 | Howell | A61B 17/221 606/127 |
| 8,574,222 | B2 | 11/2013 | Hensler et al. | |
| 8,636,722 | B2 | 1/2014 | Hensler et al. | |
| 8,845,618 | B2 | 9/2014 | Hensler et al. | |
| 2007/0219499 | A1 | 9/2007 | Hayakawa et al. | |
| 2009/0264833 | A1 | 10/2009 | Boyle, Jr. | |
| 2012/0289941 | A1 * | 11/2012 | Salehi | A61M 1/008 604/540 |
| 2014/0228817 | A1 | 8/2014 | Hensler et al. | |

* cited by examiner

ANTI-CLOG SUCTION TIP APPARATUS AND METHOD

CROSS-REFERENCE TO RELATED APPLICATION

The present patent application is a continuation of, and claims priority under 35 U.S.C. §120 to, U.S. patent application Ser. No. 14/071,602, which '602 application is a continuation-in-part patent application of, and claims priority under 35 U.S.C. §120 to:

a. U.S. continuation patent application Ser. No. 13/680,055, filed Nov. 17, 2012, which '055 application published as U.S. patent application publication no. 2013/0072911, and which '055 application is a U.S. continuation patent application of, and claims priority under 35 U.S.C. §120 to, U.S. nonprovisional patent application Ser. No. 13/596,036, filed Aug. 27, 2012, which '036 published as U.S. patent application publication no. 2013/0053828, and which '036 application is a U.S. continuation patent application of, and claims priority under 35 U.S.C. §120 to, international patent application PCT/US12/52413, filed in English on Aug. 25, 2012 and designating the United States, which international patent application is a nonprovisional of, and claims priority under 35 U.S.C. §119(e) to, each of U.S. provisional patent application 61/527,123, filed Aug. 25, 2011, and U.S. provisional patent application 61/614,915, filed Mar. 23, 2012;

b. U.S. nonprovisional patent application Ser. No. 13/596,036, filed Aug. 27, 2012, which '036 published as U.S. patent application publication no. 2013/0053828, and which '036 application is a U.S. continuation patent application of, and claims priority under 35 U.S.C. §120 to, international patent application PCT/US12/52413, filed in English on Aug. 25, 2012 and designating the United States, which international patent application is a nonprovisional of, and claims priority under 35 U.S.C. §119(e) to, each of U.S. provisional patent application 61/527,123, filed Aug. 25, 2011, and U.S. provisional patent application 61/614,915, filed Mar. 23, 2012; and c. international patent application PCT/US12/52413, filed in English on Aug. 25, 2012 and designating the United States, which international patent application is a nonprovisional of, and claims priority under 35 U.S.C. §119(e) to, each of U.S. provisional patent application 61/527,123, filed Aug. 25, 2011, and U.S. provisional patent application 61/614,915, filed Mar. 23, 2012.

The '036 application also is a nonprovisional of, and separately claims priority under 35 U.S.C. §119(e) to, each of U.S. provisional patent application 61/527,123, filed Aug. 25, 2011, and U.S. provisional patent application 61/614,915, filed Mar. 23, 2012. Any patent publication of, and any patent issuing from, any of the foregoing priority applications is hereby incorporated by reference in their entirety herein. Moreover, the disclosures of the provisionals are contained in the Appendix attached hereto, which Appendix is incorporated by reference herein.

COPYRIGHT STATEMENT

All of the material in this patent document is subject to copyright protection under the copyright laws of the United States and other countries. The copyright owner has no objection to the facsimile reproduction by anyone of the patent document or the patent disclosure, as it appears in official governmental records but, otherwise, all other copyright rights whatsoever are reserved.

BACKGROUND OF THE INVENTION

The present invention generally relates to suction tips for use during surgical procedures for the removal of biological debris, such as blood, tissue, and the like, from a surgical site. More particularly, the present invention relates to suction tips with anti-clogging capabilities for removing biological debris lodged within the suction tips.

A need exists for improvement in surgical suction tips. This, and other needs, are addressed by one or more aspects of the present invention.

SUMMARY OF THE INVENTION

The present invention includes many aspects and features. Moreover, while many aspects and features relate to, and are described in, the context of vacuum removal of biological debris in a surgical environment, the present invention is not limited to use only in vacuum removal of biological debris in a surgical environment, as will become apparent from the following summaries and detailed descriptions of aspects, features, and one or more embodiments of the present invention.

Accordingly, one aspect of the present invention relates to an anti-clog suction tip apparatus. An exemplary such apparatus includes a suction tip assembly, including a suction tip having a suction opening at a first end thereof for removing debris through suction, a hose attachment portion for attaching the suction tip assembly to a suction source, and a channel; and an ejection wire assembly, including an ejection wire disposed within the channel and an ejection tab integral with or otherwise connected to the ejection wire. Furthermore, applying a force to the ejection tab advances the ejection wire through the channel such that an end portion of the ejection wire enters the suction tip. Additionally, the end portion of the ejection wire entering the suction tip expels or dislodges debris in the suction tip through the suction opening.

In a feature of this aspect of the invention, the end portion of the ejection wire includes a ball tip.

In another feature, the suction tip assembly includes a handle.

In still another feature, the suction tip assembly includes a vacuum tunnel opening.

In yet another feature, the ejection wire is inserted into the channel through a wire insertion opening.

In a variation of this feature, wire insertion opening is threaded.

In still another feature, the ejection wire assembly further comprises an inner member disposed between the ejection wire and the ejection tab, an outer member partially surrounding the inner member, and a biasing spring.

In a variation of this feature, the outer member is threaded.

In another variation, the biasing spring biases the ejection tab away from the outer member.

In yet another feature, when dislodging debris in the suction opening, the end portion of the ejection wire does not extend more than three millimeters beyond the suction opening.

Another aspect of the present invention relates to an anti-clog suction tip apparatus. An exemplary such apparatus includes a suction tip, an interior of the suction tip defining a suction channel for the removal of debris through suction; and an ejection wire assembly removably attachable to the suction tip and transitionable between a retracted configuration and an advanced configuration. Furthermore, in the retracted configuration, the ejection wire assembly is not disposed within the suction channel, and in the advanced configuration, the ejection wire assembly is at least partially disposed within the suction channel.

Another aspect of the present invention relates to a method of clearing biological debris from a surgical site. An exemplary such method includes providing a suction tip apparatus, including an interior defining a suction channel, an ejection wire not disposed within the suction channel, and an ejection tab; attaching the suction tip apparatus to a suction source; activating the suction source to create a vacuum force in the suction tip apparatus; placing the suction tip apparatus near the debris, causing the vacuum force to pull the debris into the suction tip apparatus; applying force to the ejection tab, causing a tip of the ejection wire to enter the suction channel; and dislodging, via the tip of the ejection wire, debris clogging the suction channel.

Additional aspects of the present invention include apparatus and methods for dislodging biological debris clogged in a suction tip, as substantially shown and described herein.

In addition to the aforementioned aspects and features of the present invention, it should be noted that the present invention further encompasses the various possible combinations and subcombinations of such aspects and features. Thus, for example, any aspect may be combined with an aforementioned feature in accordance with the present invention without requiring any other aspect or feature.

BRIEF DESCRIPTION OF THE DRAWINGS

One or more preferred embodiments of the present invention now will be described in detail with reference to the accompanying drawings, wherein the same elements are referred to with the same reference numerals, and wherein.

DETAILED DESCRIPTION

Figure 1:
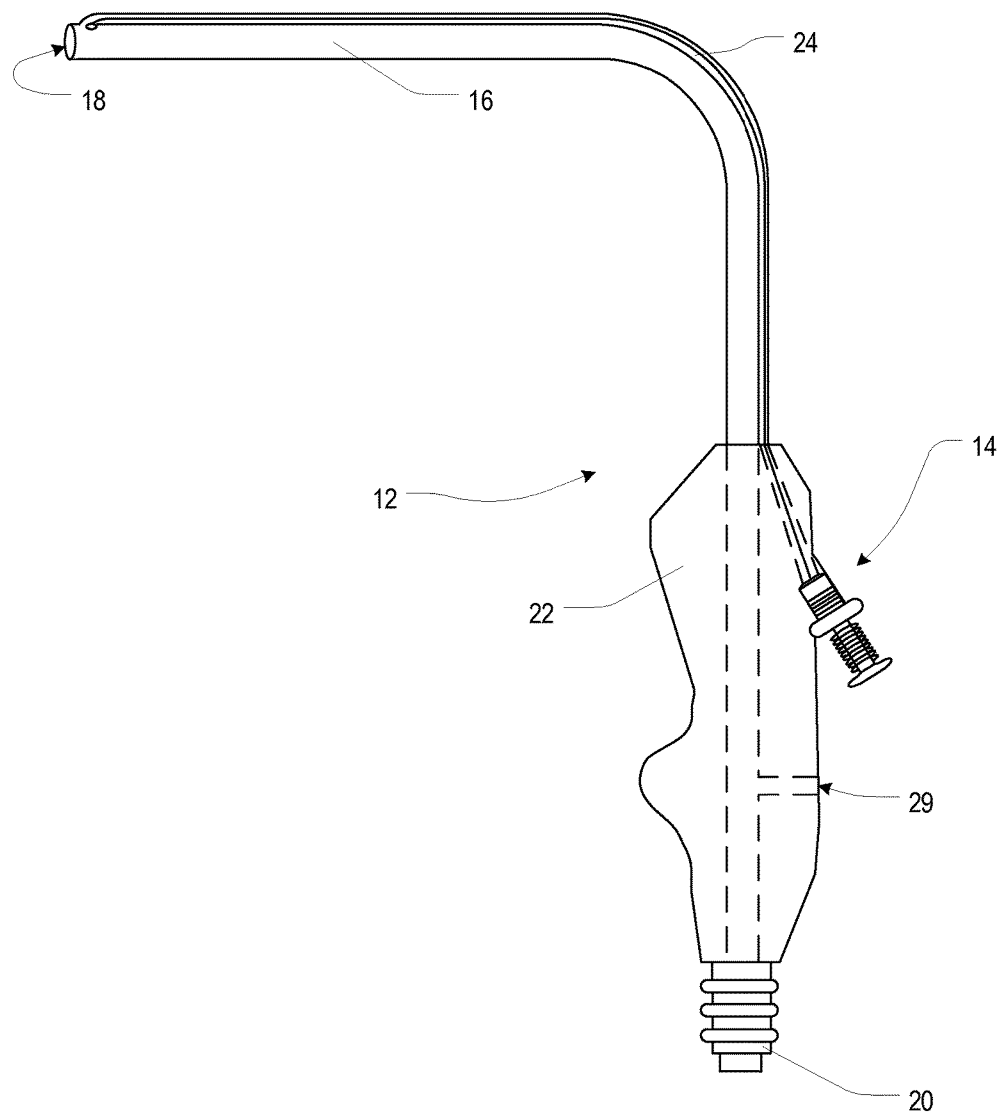
FIG. 1 is a side view of a preferred anti-clog suction tip apparatus 10 in accordance with one or more aspects of the invention.

As a preliminary matter, it will readily be understood by one having ordinary skill in the relevant art ("Ordinary Artisan") that the present invention has broad utility and application. As should be understood, any embodiment may incorporate only one or a plurality of the above-disclosed aspects of the invention and may further incorporate only one or a plurality of the above-disclosed features. Furthermore, any embodiment discussed and identified as being "preferred" is considered to be part of a best mode contemplated for carrying out the present invention. Other embodiments also may be discussed for additional illustrative purposes in providing a full and enabling disclosure of the present invention. As should be understood, any embodiment may incorporate only one or a plurality of the above-disclosed aspects of the invention and may further incorporate only one or a plurality of the above-disclosed features. Moreover, many embodiments, such as adaptations, variations, modifications, and equivalent arrangements, will be implicitly disclosed by the embodiments described herein and fall within the scope of the present invention.

Accordingly, while the present invention is described herein in detail in relation to one or more embodiments, it is to be understood that this disclosure is illustrative and exemplary of the present invention, and is made merely for the purposes of providing a full and enabling disclosure of the present invention. The detailed disclosure herein of one or more embodiments is not intended, nor is to be construed, to limit the scope of patent protection afforded the present invention, which scope is to be defined by the claims and the equivalents thereof. It is not intended that the scope of patent protection afforded the present invention be defined by reading into any claim a limitation found herein that does not explicitly appear in the claim itself.

Thus, for example, any sequence(s) and/or temporal order of steps of various processes or methods that are described herein are illustrative and not restrictive. Accordingly, it should be understood that, although steps of various processes or methods may be shown and described as being in a sequence or temporal order, the steps of any such processes or methods are not limited to being carried out in any particular sequence or order, absent an indication otherwise. Indeed, the steps in such processes or methods generally may be carried out in various different sequences and orders while still falling within the scope of the present invention. Accordingly, it is intended that the scope of patent protection afforded the present invention is to be defined by the appended claims rather than the description set forth herein.

Additionally, it is important to note that each term used herein refers to that which the Ordinary Artisan would understand such term to mean based on the contextual use of such term herein. To the extent that the meaning of a term used herein—as understood by the Ordinary Artisan based on the contextual use of such term—differs in any way from any particular dictionary definition of such term, it is intended that the meaning of the term as understood by the Ordinary Artisan should prevail.

Regarding applicability of 35 U.S.C. §112, ¶6, no claim element is intended to be read in accordance with this statutory provision unless the explicit phrase "means for" or "step for" is actually used in such claim element, whereupon this statutory provision is intended to apply in the interpretation of such claim element.

Furthermore, it is important to note that, as used herein, "a" and "an" each generally denotes "at least one," but does not exclude a plurality unless the contextual use dictates otherwise. Thus, reference to "a picnic basket having an apple" describes "a picnic basket having at least one apple" as well as "a picnic basket having apples." In contrast, reference to "a picnic basket having a single apple" describes "a picnic basket having only one apple."

When used herein to join a list of items, "or" denotes "at least one of the items," but does not exclude a plurality of items of the list. Thus, reference to "a picnic basket having cheese or crackers" describes "a picnic basket having cheese without crackers", "a picnic basket having crackers without cheese", and "a picnic basket having both cheese and crackers." Finally, when used herein to join a list of items, "and" denotes "all of the items of the list." Thus, reference to "a picnic basket having cheese and crackers" describes "a picnic basket having cheese, wherein the picnic basket further has crackers," as well as describes "a picnic basket having crackers, wherein the picnic basket further has cheese."

Referring now to the drawings, one or more preferred embodiments of the present invention are next described. The following description of one or more preferred embodiments is merely exemplary in nature and is in no way intended to limit the invention, its implementations, or uses.

FIG. 1 is a side view of a preferred anti-clog suction tip apparatus 10 in accordance with one or more aspects of the invention. The anti-clog suction tip apparatus 10 is adapted to attach to a hose having a suction source attached thereto, and is useful during surgical procedures for the removal of blood, tissue, and the like, from a surgical site. The anti-clog suction tip apparatus 10 comprises a suction tip assembly 12 and an ejection wire assembly 14.

Figure 2:
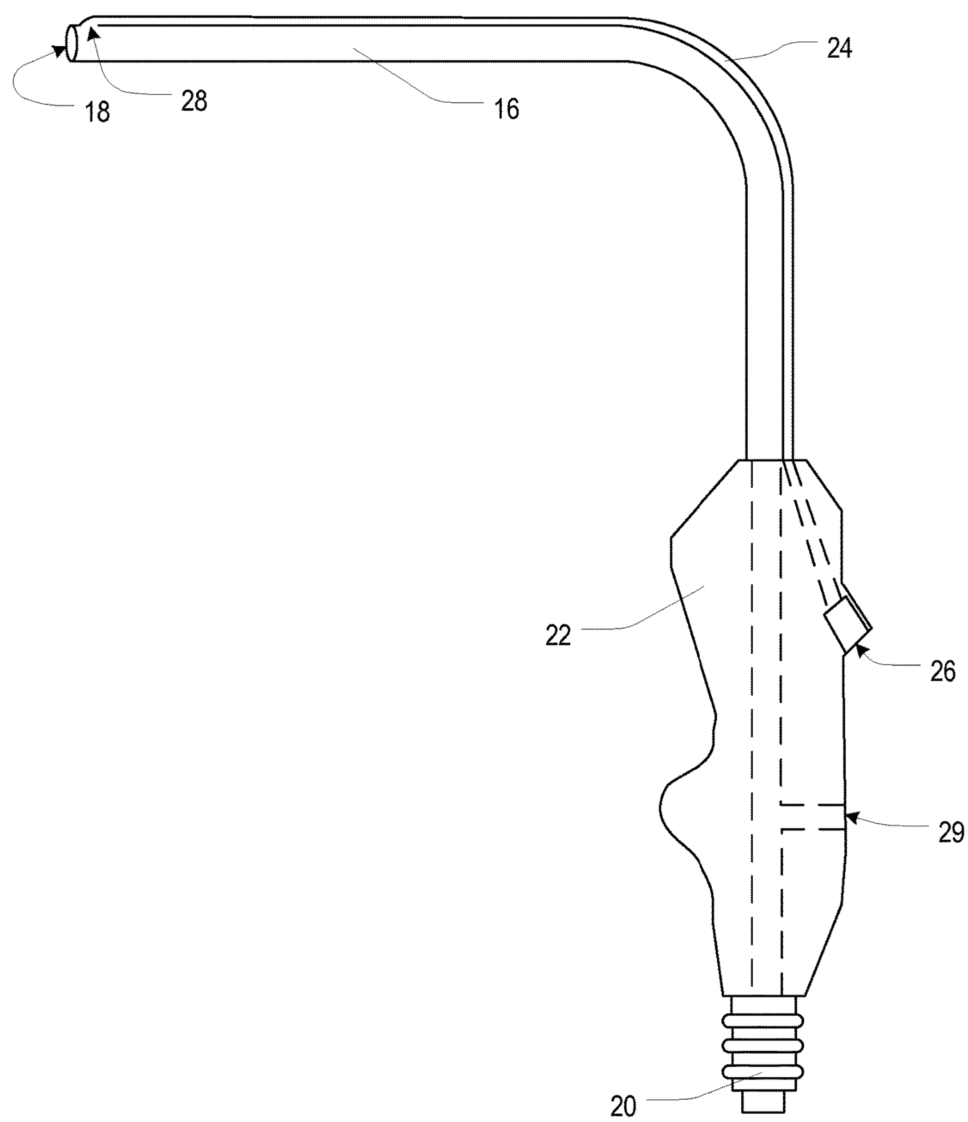
FIG. 2 is a side view of suction tip assembly shown as part of the anti-clog suction tip apparatus 10 of FIG. 1.
Figure 3:
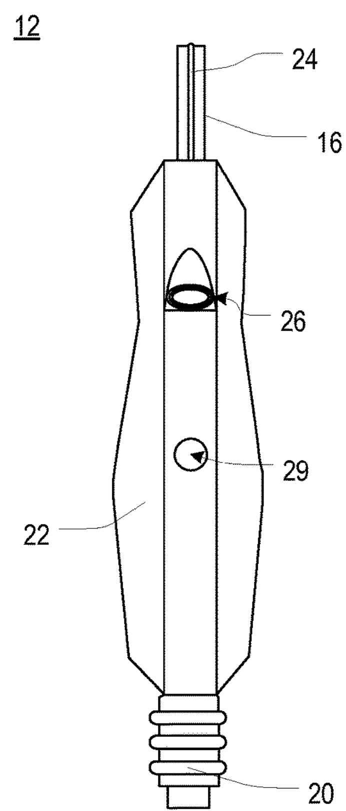
FIG. 3 is a back view of the suction tip assembly of FIG. 2.
Figure 4:
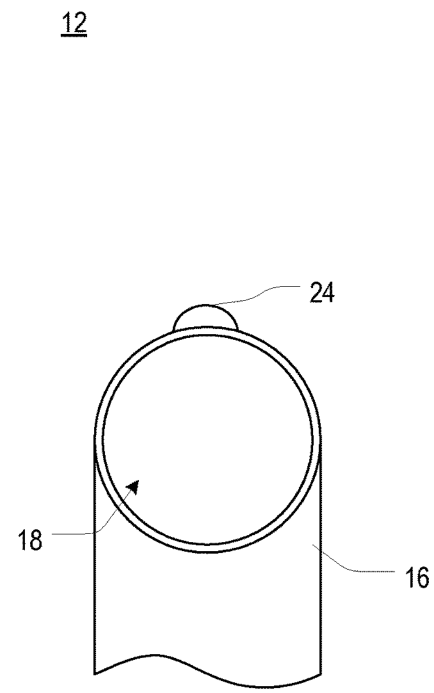
FIG. 4 is an enlarged front view of a portion of the suction tip assembly of FIG. 2.

FIG. 2 is a side view of suction tip assembly 12 shown as part of the anti-clog suction tip apparatus 10 of FIG. 1. FIG. 3 is a back view of the suction tip assembly 12 of FIG. 2. FIG. 4 is an enlarged front view of a portion of the suction tip assembly 12 of FIG. 2.

As seen in FIG. 2-4, the suction tip assembly 12 includes a suction tip 16 having a suction opening 18 at a distal end thereof and a hose attachment portion 20 at a proximal end thereof. The suction tip assembly 12 further includes a handle portion 22 and an ejection wire channel 24. At least a portion of the ejection wire channel 24 abuts the suction tip 16. The ejection wire channel 24 extends from a wire insertion opening 26 located on the handle 22 to a wire exit opening 28 on the suction tip 16 proximate the suction opening 18. In at least one preferred embodiment, the wire insertion opening 26 is a threaded opening. Furthermore, in at least one preferred embodiment, the handle 22 includes a vacuum tunnel opening 29. Covering the vacuum tunnel opening 29 during use of the anti-clog suction tip apparatus 10 increases the vacuum pressure exerted at the suction opening 18.

Figure 5A:
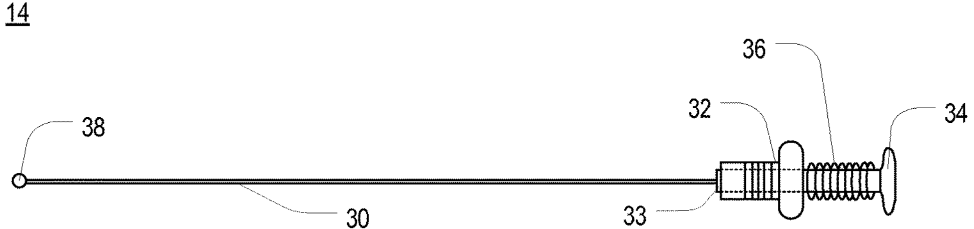
FIGS. 5A and 5B are side views of the ejection wire assembly shown as part of the anti-clog suction tip assembly 10 of FIG. 1.
Figure 5B:
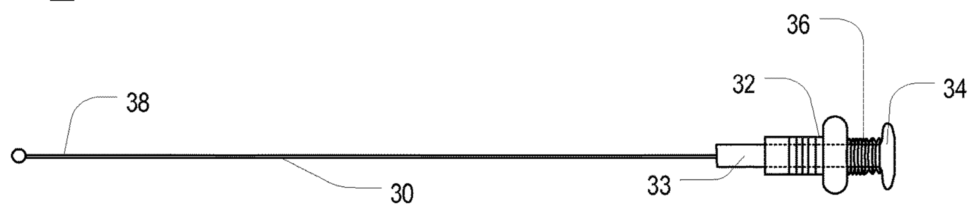

FIGS. 5A and 5B are side views of the ejection wire assembly 14 shown as part of the anti-clog suction tip assembly 10 of FIG. 1.

FIG. 5A illustrates the ejection wire assembly 14 in a retracted position. FIG. 5B illustrates the ejection wire assembly 14 in an advanced position.

The ejection wire assembly 14 comprises an ejection wire 30, an outer member 32, an inner member 33, an ejection tab 34, and a biasing spring 36. In one or more preferred embodiments, the ejection wire 30 comprises a semi-rigid cable extending from the inner member 33. The ejection wire 30 includes a small ball tip 38 at the end thereof to prevent unintended injury during use.

As seen in FIGS. 5A and 5B, a first end of the inner member 33 is integral with the ejection tab 34 and a second end of the inner member 33 is attached to the ejection wire 30. Furthermore, the outer member 32 encompasses at least a portion the inner member 33 (shown in dotted lines). Finally, the biasing spring 36 encircles a portion of the inner member 33 and is configured to bias the ejection tab 34 away from the outer member 32.

In some alternative embodiments, the ejection tab is formed separately from and is connected to the ejection wire.

As seen best in FIG. 5B, assuming the outer member 32 is immobile, as force is applied to the ejection tab 34, the ejection tab 34, the inner member 33, and the ejection wire 30 advance in the direction of the applied force and the biasing spring 36 contracts. Upon removal of the force, the biasing spring 36 returns to its relaxed position, forcing the ejection tab 34, the inner member 33 and the ejection wire 30 back to the retracted position of FIG. 5A.

Returning now to FIG. 1, the ejection wire assembly 14 is shown threadably attached to the suction tip assembly 12 and in a retraced position. To affix to the ejection wire assembly 14 to the suction tip assembly 12, the ejection wire 30 is first inserted into the wire insertion opening 26 on the handle. Next, the ejection wire 30 is slid forward to occupy the ejection wire channel 24. Preferably, only upon full insertion of the ejection wire 30 into the ejection wire channel 24 can the outer member 32 be threadably secured to the cable insertion opening 26 in the handle 22.

Figure 6:
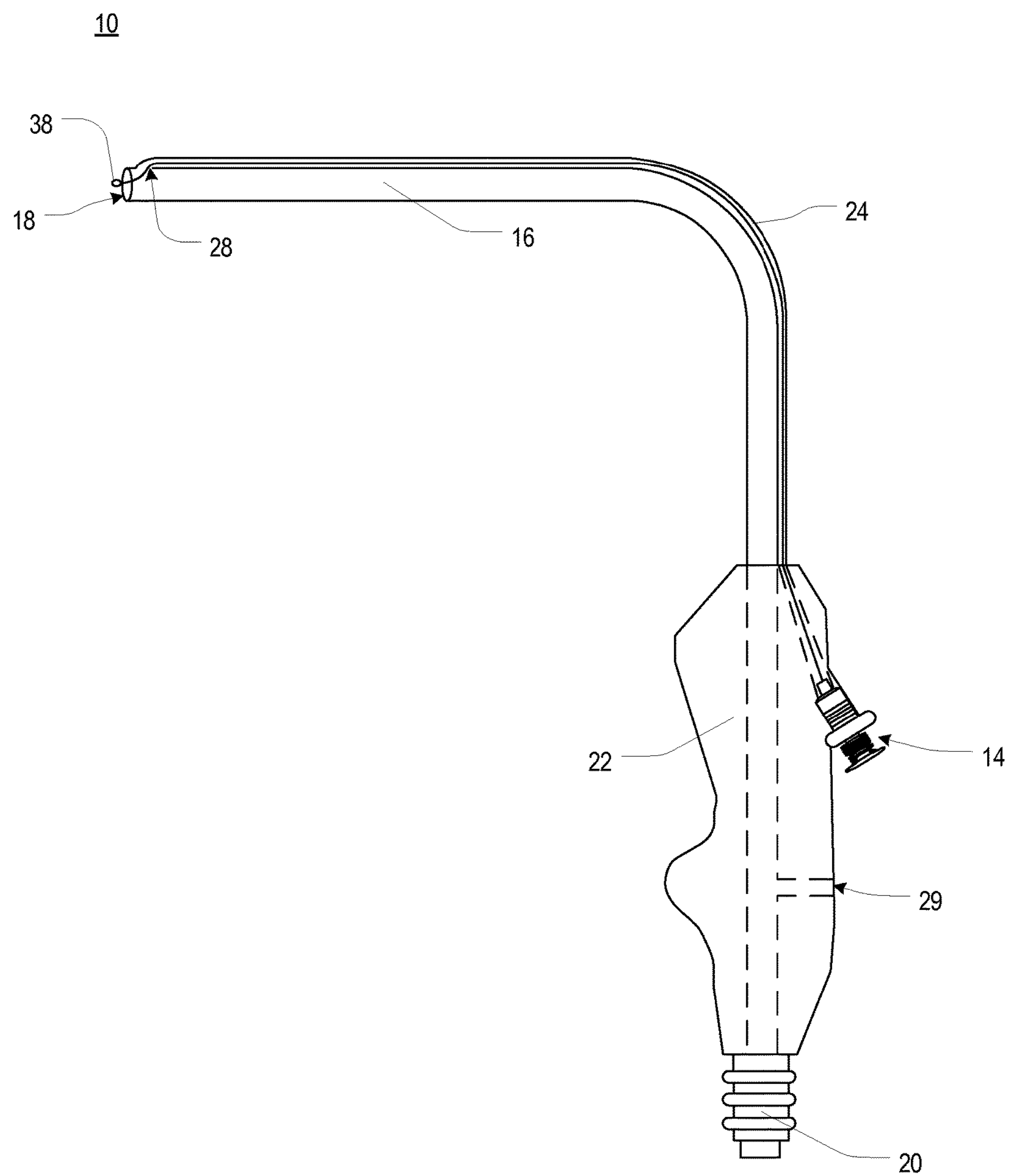
FIG. 6 is a side view of the anti-clog suction tip apparatus 10 of FIG. 1, illustrating operation of the ejection wire assembly when installed in the anti-clog suction tip apparatus, the ejection wire assembly being shown in an advanced position.
Figure 7C:
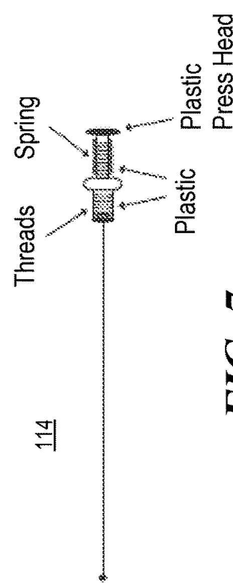
FIGS. 7*a*-7*d* and 8*a*-8*b* show additional views of another preferred anti-clog suction tip apparatus in accordance with one or more aspects of the invention.
Figure 7D:
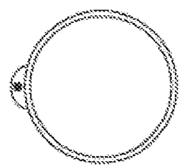
Figure 7B:
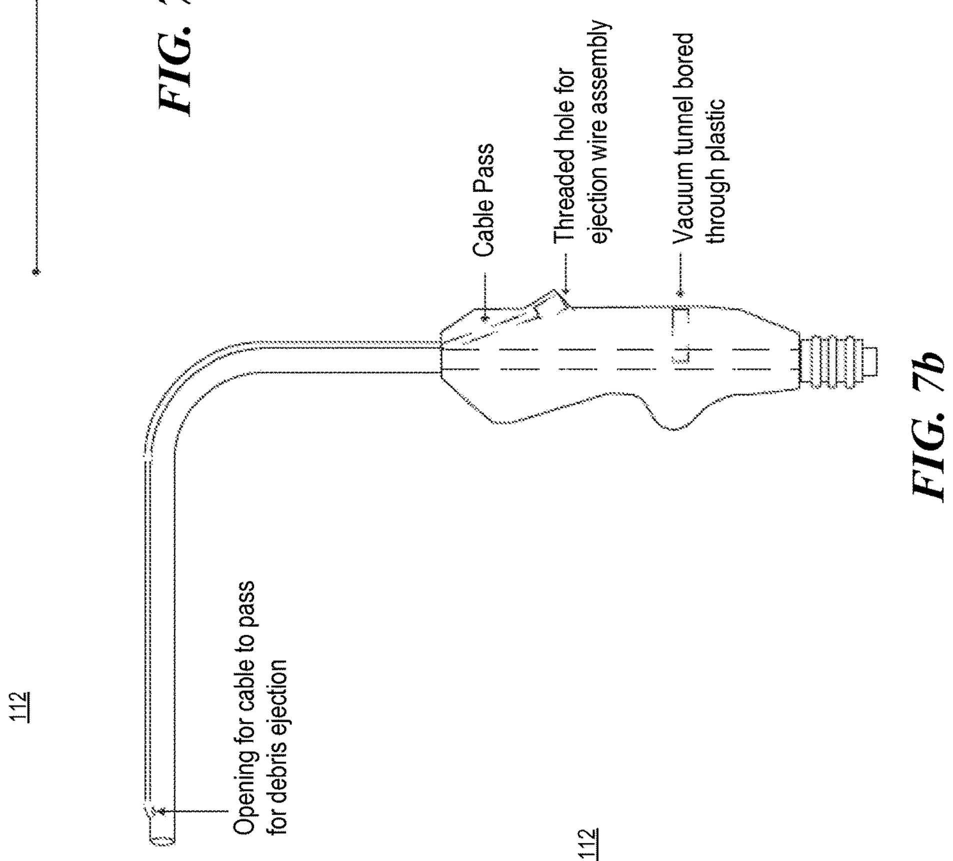
Figure 7A:
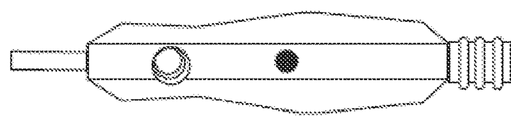
Figure 8B:
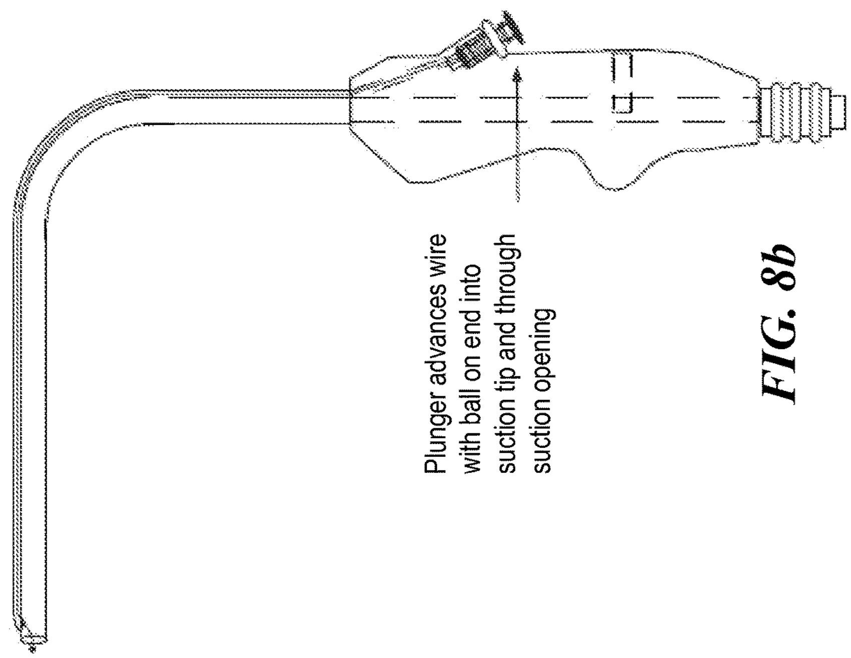
Figure 8A:
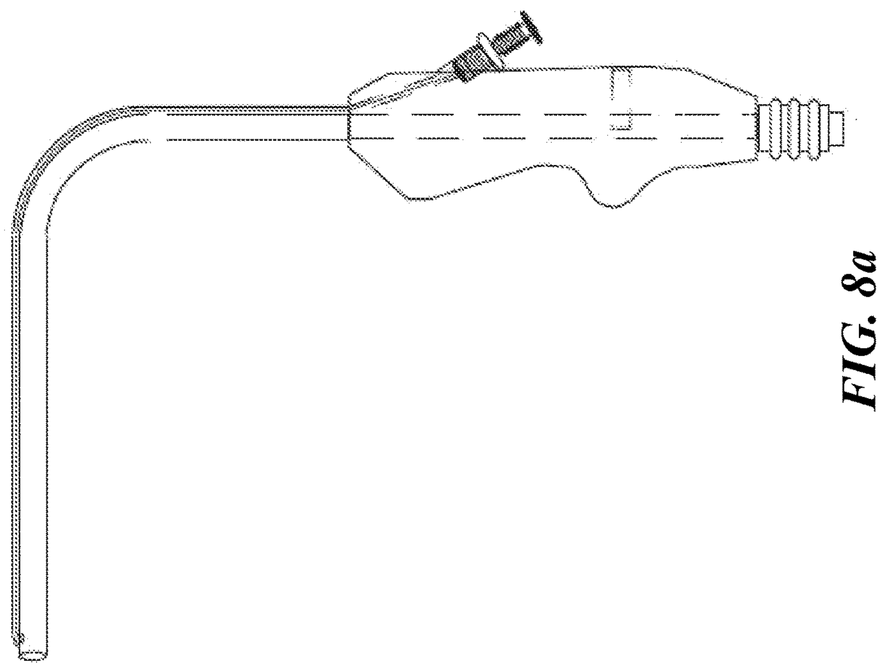

FIG. 6 is a side view of the anti-clog suction tip apparatus 10 of FIG. 1, showing the ejection wire assembly 14 secured to the suction tip assembly 12 in an advanced position. As discussed previously with reference to FIGS. 5A and 5B, the ejection wire assembly 14 is placed in an advanced position by applying force to the ejection tab 34. As force is applied, the ejection wire 30 moves forward.

When the ejection wire 30 is advanced forward, the ball tip 38 passes through the wire exit opening 28 into the suction tip 16 and dislodges any biological debris clogging the suction tip 16, such as blood, tissue, and the like, to unclog the suction tip 16. Such debris may be expelled through the through the suction opening 18. In at least one preferred embodiment, the ball tip 38 does not extend more than three millimeters beyond (protract from) the suction opening 18 when the ejection wire 30 is fully advanced by depression of the ejection tab 34.

To use the anti-clog suction tip apparatus 10 in a surgical environment, sterile packaging in which the anti-clog suction tip apparatus 10 is provided is opened by sterile technique. The anti-clog suction tip apparatus 10 is removed from the packaging and placed on a sterile table to await use by a surgeon or surgical assistant. A hose attached to a suction source is secured to the hose attachment portion 20. Upon activation of the suction source, a vacuum is produced within the suction tip 16, enabling the suction tip 16 to remove biological debris, such as blood, tissue, and the like, from the operation site.

During the course of use, it is believed that the suction tip 16 is likely to become clogged with biological debris. Immediate ejection of the debris is oftentimes necessary in the surgical environment. To remove unwanted debris from the suction tip 16, the user applies force to the ejection tab 34, causing the ejection wire 30 to advance from the ejection wire channel 24, through the wire exit opening 28, and expel the debris clogged in the suction tip 16 through the suction opening 18. Some debris that is dislodges then may also be suctioned. To retract the ejection wire 30, the user removes the applied force from the ejection tab 34. The biasing spring 36 causes the ejection tab 34 to return to its initial position, thus retracting the ejection wire 30. When retracted, the ejection wire 30, and in particular the ball tip 38, is retained within the wire channel 24 and does not obstruct normal suctioning of the debris during use of the apparatus 10.

An added advantage of an anti-clog suction tip apparatus 10 in accordance with one or more embodiments of the present invention is the location of the ejection wire assembly 14. More particularly, the ejection tab 34 is located on the handle 22 and not in the user's line of sight and thus does not obstruct the user's view during a surgical procedure.

In one or more preferred embodiments, the anti-clog suction tip apparatus 10 is intended to be disposed after a single surgical use. After use, the anti-clog suction tip apparatus 10 will include biological and potentially hazardous debris, and thus, should be disposed according to any applicable HAZMAT protocol.

In at least one preferred embodiment, a secondary wire is supplied to be inserted into the suction tip 16 through the suction opening 18 to more completely clear debris if the ejection wire 30 is unable to completely expel the debris. It is further contemplated that alternative ejection wires may be included that have other sizes, dimensions, and profiles of ball tips, and that have wires of different diameters and different rigidity characteristics.

FIGS. 7*a*-7*d* and 8*a*-8*b* show additional views of another preferred anti-clog suction tip apparatus 110 in accordance with one or more aspects of the invention, which apparatus 110 is similar in appearance to apparatus 10. The anti-clog suction tip apparatus 110 comprises a suction tip assembly 112 and an ejection wire assembly 114.

Based on the foregoing description, it will be readily understood by those persons skilled in the art that the present invention is susceptible of broad utility and application. Many embodiments and adaptations of the present invention other than those specifically described herein, as well as many variations, modifications, and equivalent arrangements, will be apparent from or reasonably suggested by the present invention and the foregoing descriptions thereof, without departing from the substance or scope of the present invention.

Accordingly, while the present invention has been described herein in detail in relation to one or more preferred embodiments, it is to be understood that this disclosure is only illustrative and exemplary of the present invention and is made merely for the purpose of providing a full and enabling disclosure of the invention. The foregoing disclosure is not intended to be construed to limit the present invention or otherwise exclude any such other embodiments, adaptations, variations, modifications or equivalent arrangements, the present invention being limited only by the claims appended hereto and the equivalents thereof.

What is claimed is:

1. A method of clearing debris from a surgical site, comprising the steps of:

(a) attaching a suction tip apparatus to a suction source, the suction tip apparatus comprising,
   (i) a suction tip at a distal end of the apparatus having a suction opening and having a suction channel for the removal of debris through suction applied at the suction opening,
   (ii) a handle portion for handling of the apparatus,
   (iii) an ejection wire channel extending from a distal end of the handle portion and opening into the suction channel of the suction tip proximate the suction opening of the suction tip,
   (iv) an ejection wire extending within the ejection wire channel,
   (v) a spring element, and
   (vi) a manually operated control located on and extending within a threaded opening of the handle portion;
(b) activating the suction source to apply suction at the suction opening of the suction tip;
(c) placing the suction tip near the debris causing the debris to be suctioned into the suction opening of the suction tip; and
(d) while handling the apparatus, transitioning the ejection wire from a retracted position, in which retracted position the ejection wire is retained within the ejection wire channel and does not obstruct suctioning of debris through the suction channel of the suction tip, toward an advanced position, in which advanced position the ejection wire extends from the ejection wire channel through the suction channel of the suction tip to the suction opening, whereby advancement of the ejection wire expels debris from the suction channel, said transitioning including operating the manually operated control in opposition to the spring element, which biases the ejection wire toward the retracted position.

2. The method of claim 1, wherein the ejection wire channel extends from the handle portion to the suction tip.

3. The method of claim 1, wherein the handle portion comprises a vacuum tunnel opening, and wherein the manually operated control is located on the same side of the handle portion as the vacuum tunnel opening.

4. The method of claim 3, wherein the manually operated control is located between the vacuum tunnel opening and the distal end of the handle portion.

5. The method of claim 1, wherein the manually operated control comprises an ejection tab.

6. The method of claim 5, wherein transitioning the ejection wire from the retracted position toward the advanced position comprises manually depressing the ejection tab.

7. The method of claim 6, further comprising returning the ejection wire to the retracted position from the advanced position by ceasing to depress the manually operated control.

8. The method of claim 6, wherein the ejection tab is manually depressed in a direction that is angled toward the distal end of the handle portion.

9. The method of claim 8, wherein the ejection tab is located behind a proximal end of the ejection wire relative to the direction of depression of the ejection tab.

10. A method of clearing debris from a surgical site, comprising the steps of:

(a) attaching a suction tip apparatus to a suction source, the suction tip apparatus comprising,
   (i) a suction tip at a distal end of the apparatus having a suction opening and having a suction channel for the removal of debris through suction applied at the suction opening,
   (ii) a handle portion for handling of the apparatus,
   (iii) an ejection wire channel extending from a distal end of the handle portion and opening into the suction channel of the suction tip proximate the suction opening of the suction tip,
   (iv) an ejection wire extending within the ejection wire channel,
   (v) a spring element, and
   (vi) a manually operated control located on the handle portion;
(b) activating the suction source to apply suction at the suction opening of the suction tip;
(c) placing the suction tip near the debris causing the debris to be suctioned into the suction opening of the suction tip; and
(d) while handling the apparatus, transitioning the ejection wire from a retracted position, in which retracted position the ejection wire is retained within the ejection wire channel and does not obstruct suctioning of debris through the suction channel of the suction tip, toward an advanced position, in which advanced position the ejection wire extends from the ejection wire channel through the suction channel of the suction tip to the suction opening, whereby advancement of the ejection wire expels debris from the suction channel, said transitioning including operating the manually operated control in opposition to the spring element, which biases the ejection wire toward the retracted position;

(e) wherein the manually operated control comprises an ejection tab; and (f) wherein the ejection tab extends within a threaded opening of the handle portion.

11. The method of claim 10, further comprising removing the ejection wire from the apparatus through the threaded opening of the handle portion.

12. The method of claim 1, wherein the ejection wire comprises a cable.

13. The method of claim 1, wherein the handle portion is plastic.

14. The method of claim 1, wherein the ejection wire occupies the ejection wire channel.

15. The method of claim 1, wherein the distal end of the ejection wire does not extend more than three millimeters beyond the suction opening when the ejection wire is fully advanced by depression of the ejection tab.

16. The method of claim 1, wherein the manually operated control comprises a plunger that has a press head and that is depressible in a direction angled toward the distal end of the handle portion.

17. A method of clearing debris from a surgical site, comprising the steps of:

(a) attaching a suction tip apparatus to a suction source, the suction tip apparatus comprising, (i) a suction tip at a distal end of the apparatus having a suction opening and having a suction channel for the removal of debris through suction applied at the suction opening, (ii) a handle portion for handling of the apparatus, (iii) an ejection wire channel extending from a distal end of the handle portion and opening into the suction channel of the suction tip proximate the suction opening of the suction tip, (iv) an ejection wire extending within the ejection wire channel, (v) a spring element, and (vi) a manually operated control located on the handle portion;

(b) activating the suction source to apply suction at the suction opening of the suction tip;

(c) placing the suction tip near the debris causing the debris to be suctioned into the suction opening of the suction tip; and (d) while handling the apparatus, transitioning the ejection wire from a retracted position, in which retracted position the ejection wire is retained within the ejection wire channel and does not obstruct suctioning of debris through the suction channel of the suction tip, toward an advanced position, in which advanced position the ejection wire extends from the ejection wire channel through the suction channel of the suction tip to the suction opening, whereby advancement of the ejection wire expels debris from the suction channel, said transitioning including operating the manually operated control in opposition to the spring element, which biases the ejection wire toward the retracted position;

(e) wherein the manually operated control comprises a plunger that has a press head and that is depressible in a direction angled toward the distal end of the handle portion; and (f) wherein the plunger extends within a threaded opening of the handle portion.

18. The method of claim 17, wherein the press head of the plunger is located behind a proximal end of the ejection wire relative to the direction of depression of the plunger.

19. The method of claim 18, wherein the distal end of the ejection wire does not extend more than three millimeters beyond the suction opening when the ejection wire is fully advanced by depression of the plunger.

20. The method of claim 1, further comprising, while handling the apparatus, returning the ejection wire to the retracted position by ceasing to operate the manually operated control in opposition to the spring element such that the spring element returns the ejection wire to the retracted position.

* * * * *